(12) United States Patent
Arcilla et al.

(10) Patent No.: US 9,186,475 B2
(45) Date of Patent: Nov. 17, 2015

(54) STORAGE DEVICE FOR A VENTILATION MASK

(75) Inventors: Mabini Arcilla, San Diego, CA (US); Gardner Kimm, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 594 days.

(21) Appl. No.: 13/508,419

(22) PCT Filed: Oct. 26, 2010

(86) PCT No.: PCT/IB2010/054843
§ 371 (c)(1),
(2), (4) Date: May 7, 2012

(87) PCT Pub. No.: WO2011/058472
PCT Pub. Date: May 19, 2011

(65) Prior Publication Data
US 2012/0227745 A1    Sep. 13, 2012

Related U.S. Application Data

(60) Provisional application No. 61/260,103, filed on Nov. 11, 2009.

(51) Int. Cl.
*A61M 16/06* (2006.01)
*A61L 2/10* (2006.01)

(52) U.S. Cl.
CPC . *A61M 16/06* (2013.01); *A61L 2/10* (2013.01); *A61M 2205/11* (2013.01); *A61M 2209/06* (2013.01)

(58) Field of Classification Search
CPC ............ A61L 2/10; A61L 2/16; A61M 16/06
See application file for complete search history.

(56) References Cited

U.S. PATENT DOCUMENTS

| | | | |
|---|---|---|---|
| 4,940,049 A | 7/1990 | Kirchgeorg | |
| 5,029,252 A * | 7/1991 | Ameseder | 250/455.11 |
| 7,225,559 B1 * | 6/2007 | Padilla | 34/202 |
| 7,798,332 B1 * | 9/2010 | Brunet | 206/570 |
| 8,746,251 B2 * | 6/2014 | Besch et al. | 128/207.18 |
| 2002/0007832 A1 | 1/2002 | Doherty | |
| 2005/0254992 A1* | 11/2005 | Jenkins et al. | 422/24 |
| 2006/0237007 A1 | 10/2006 | Quest | |
| 2009/0071480 A1* | 3/2009 | Adams | 128/204.18 |
| 2009/0292258 A1 | 11/2009 | Turner | |

FOREIGN PATENT DOCUMENTS

| | | |
|---|---|---|
| CN | 1666781 A | 9/2005 |
| JP | S59187541 A | 10/1984 |
| JP | 3116516 | 12/1991 |

(Continued)

*Primary Examiner* — Regina M Yoo

(57) ABSTRACT

A ventilation mask storage device (300, 400, 500) includes a first (310, 410, 510) and second body members (320, 420, 520); a hinge (330, 430, 530) connecting the first and second body members so the first and second body members can be brought together to define an enclosed space (305, 405, 505) for receiving a ventilation mask (10); a clasp (340, 440, 540) connected to the first and second body members to hold the first and second body members together when the clasp is engaged; an aperture (300, 400, 500) in at least one of the first and second body members to permit a circuit (15) to be connected to the ventilation mask when it is disposed within the enclosed space; and a connector (360, 460, 560) provided with at least one of the first and second body members to attach the device to a ventilator or ventilator cart.

20 Claims, 12 Drawing Sheets

(56) References Cited

FOREIGN PATENT DOCUMENTS

| | | |
|---|---|---|
| JP | 2003024419 A | 1/2003 |
| JP | 2005111034 A | 4/2005 |
| JP | 2006500158 A | 1/2006 |
| JP | 2009039202 A | 2/2009 |

* cited by examiner

STORAGE DEVICE FOR A VENTILATION MASK

This invention pertains to ventilation masks, and in particular, to storage devices for ventilation masks.

Ventilators are used in a variety of settings. In a hospital, a patient may be ventilated as part of their medical care. At home, an increasing number of people use continuous positive air pressure (CPAP) machines to address sleep apnea problems. A ventilator interfaces with an individual via ventilation mask which is connected via a ventilator circuit (typically a flexible hose) to the ventilator machine.

FIG. 1 illustrates an example of a patient with a ventilation mask 10 and a ventilator circuit 15 connecting ventilation mask 10 to the ventilator (not shown in FIG. 1). Ventilation mask 10 includes two connectors 12 configured for a strap 14 or straps (e.g., straps fitted with VELCRO® or other hook-and-loop type attachments) to pass therethrough and thereby secure ventilation mask 10 to the patient's head.

FIG. 2 shows a more detailed illustration of another embodiment of a ventilation mask 10.

Patients using ventilators typically may have periods of times when they are removed from the ventilator. For example, some patients are only ventilated during the night as a means of resting the respiratory muscles. Patients may also be temporarily disconnected from the ventilator in order to eat, drink, or undergo a medical procedure.

However, during periods in between ventilator use, there is no safe and convenient place to store the mask. During these periods without ventilation, ventilation mask 10 and attached ventilator circuit 15 is typically placed on a bedside table, looped around support arm or rail of the ventilator or a ventilator cart on which the ventilator is provided, or placed somewhere else at the side of the bed. Loosely placing ventilation mask 10 and attached ventilator circuit 15 at the bedside leaves the mask susceptible to contamination (e.g., falling on the floor, coming into contact with a contaminated surface, or exposure to airborne contaminants). In addition, should ventilation mask 10 become contaminated, there are no easy methods for disinfection. In current practice, clinicians have been known to use less than satisfactory solutions such as placing ventilation mask 10 in a surgical glove, or reusing a plastic packaging bag, in an attempt to keep ventilation mask 10 clean.

Accordingly, it would be desirable to provide an arrangement for keeping a ventilation mask in a more sterile setting when it is temporarily not in use.

In one aspect of the invention, a storage device is provided for a ventilation mask when the ventilation mask is not in use. The storage device comprises: a first body member; a second body member; a hinge connecting the first body member to the second body member so that the first body member and second body member can be brought together to define a substantially enclosed space therebetween that is configured to receive the ventilation mask; a clasping device connected to the first body member and second body member to hold the first body member and second body member together when the clasping device is engaged; an aperture in at least one of the first and second body members configured to permit a circuit to be connected to the ventilation mask when the ventilation mask is disposed within the substantially enclosed space; and a connector provided with at least one of the first and second body members and configured to attach the device to one of a ventilator and a ventilator cart.

In another aspect of the invention, another storage device is provided for a ventilation mask when the ventilation mask is not in use. The storage device comprises: a body member having a first side and a second side, the first side defining a recess therein that is configured to receive and hold a ventilation mask; and a connector provided on the second side of the body member that is configured to attach the device to one of a ventilator and a ventilator cart.

FIGS. 4A-D illustrate another embodiment of a storage device for a ventilation mask.

Figure 5A:
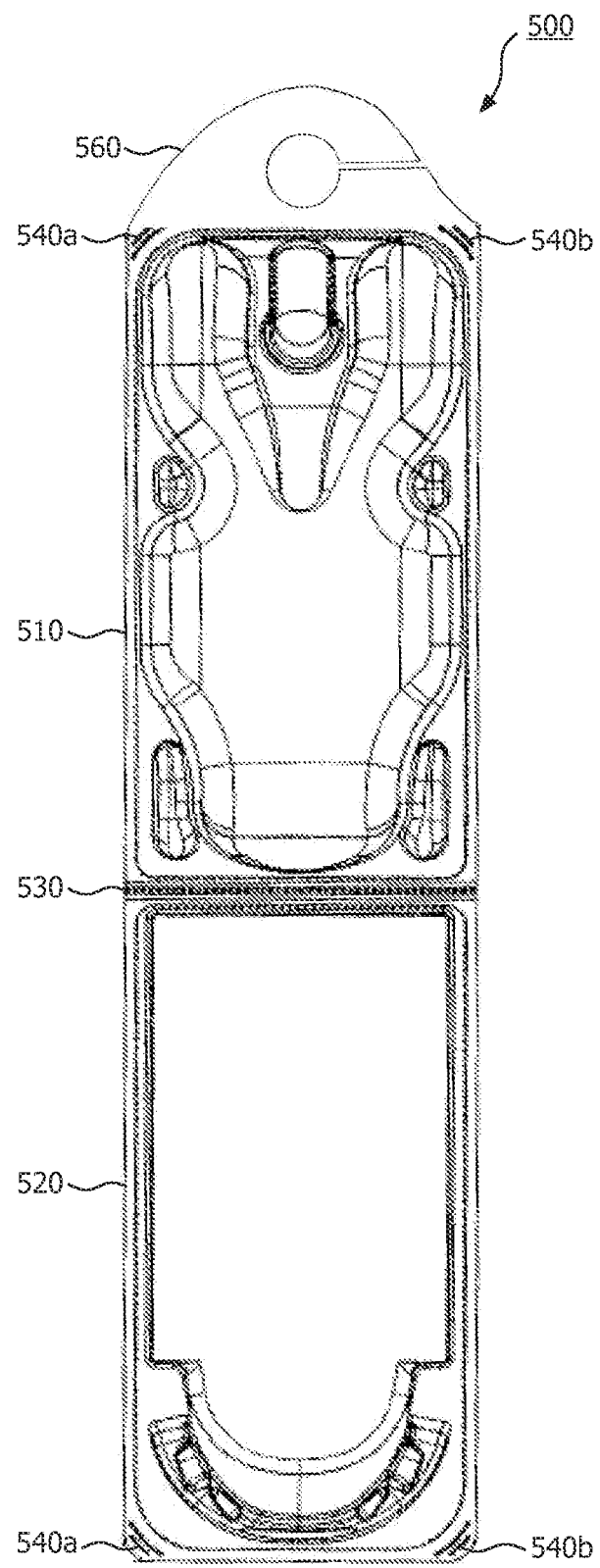
Figure 5B:
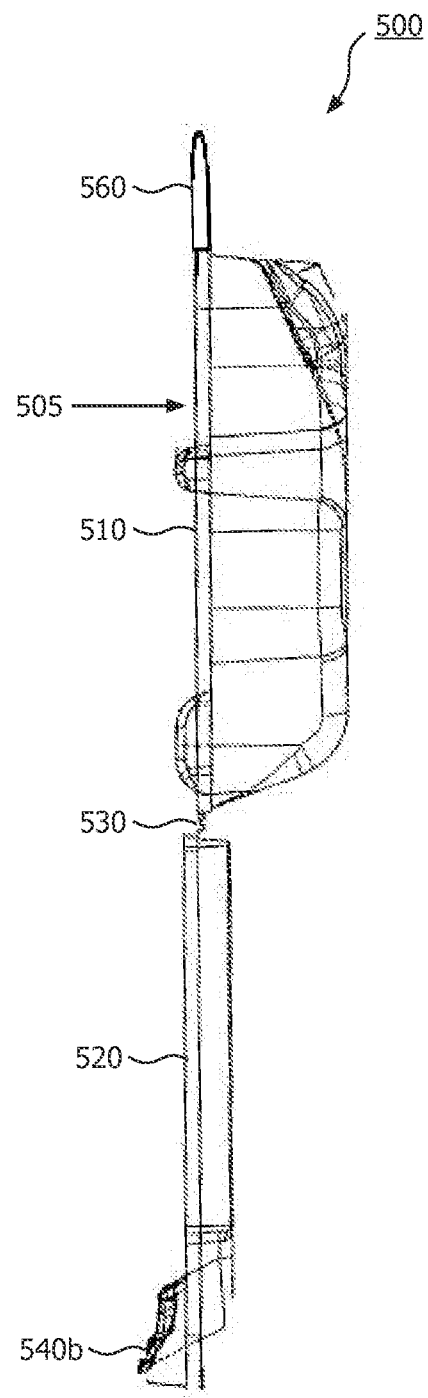

FIGS. 5A-B illustrate yet another embodiment of a storage device for a ventilation mask.

Figure 6:
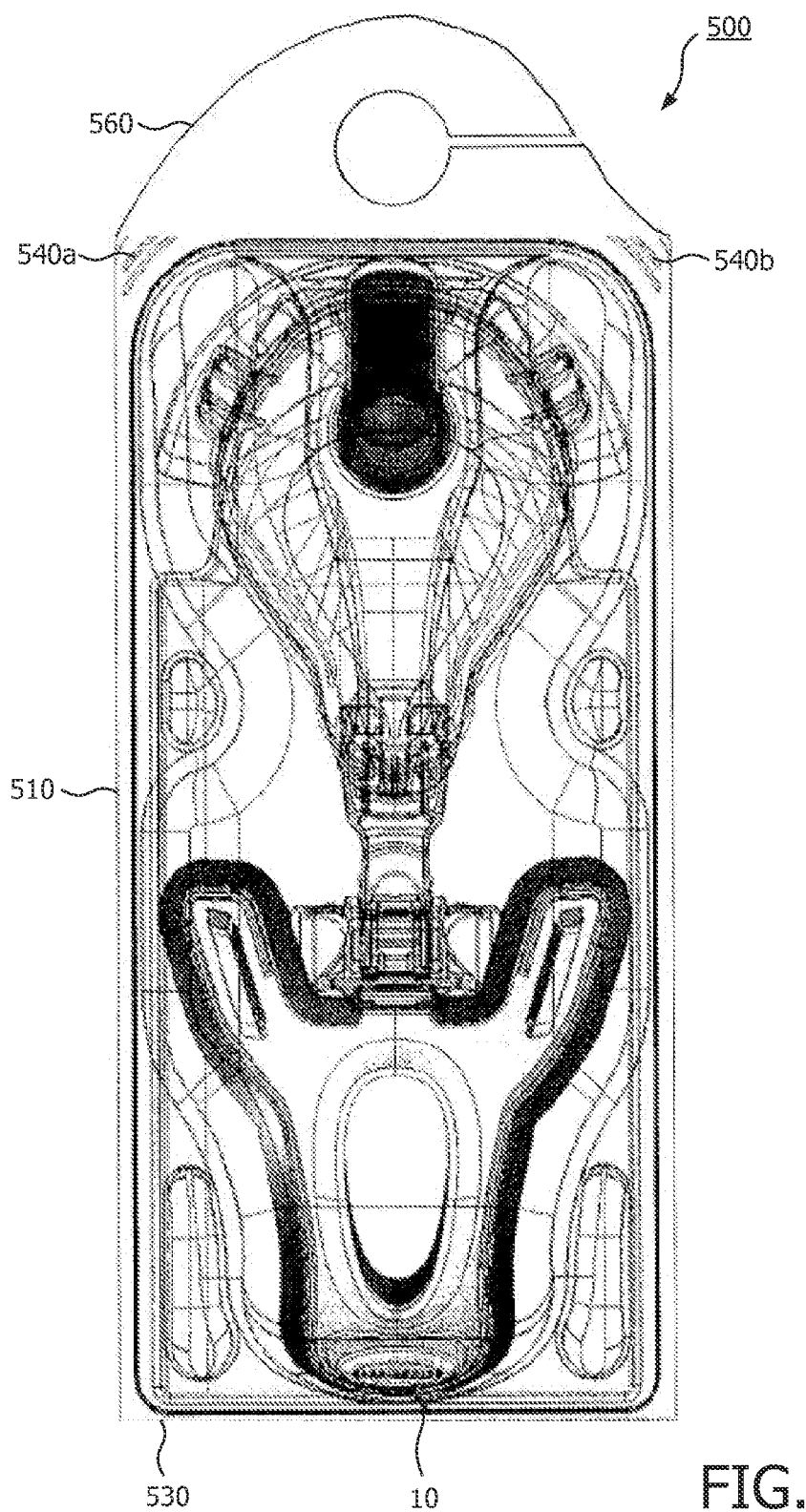

FIG. 6 is another view of the ventilation mask storage device of FIGS. 5A-B.

Figure 7A:
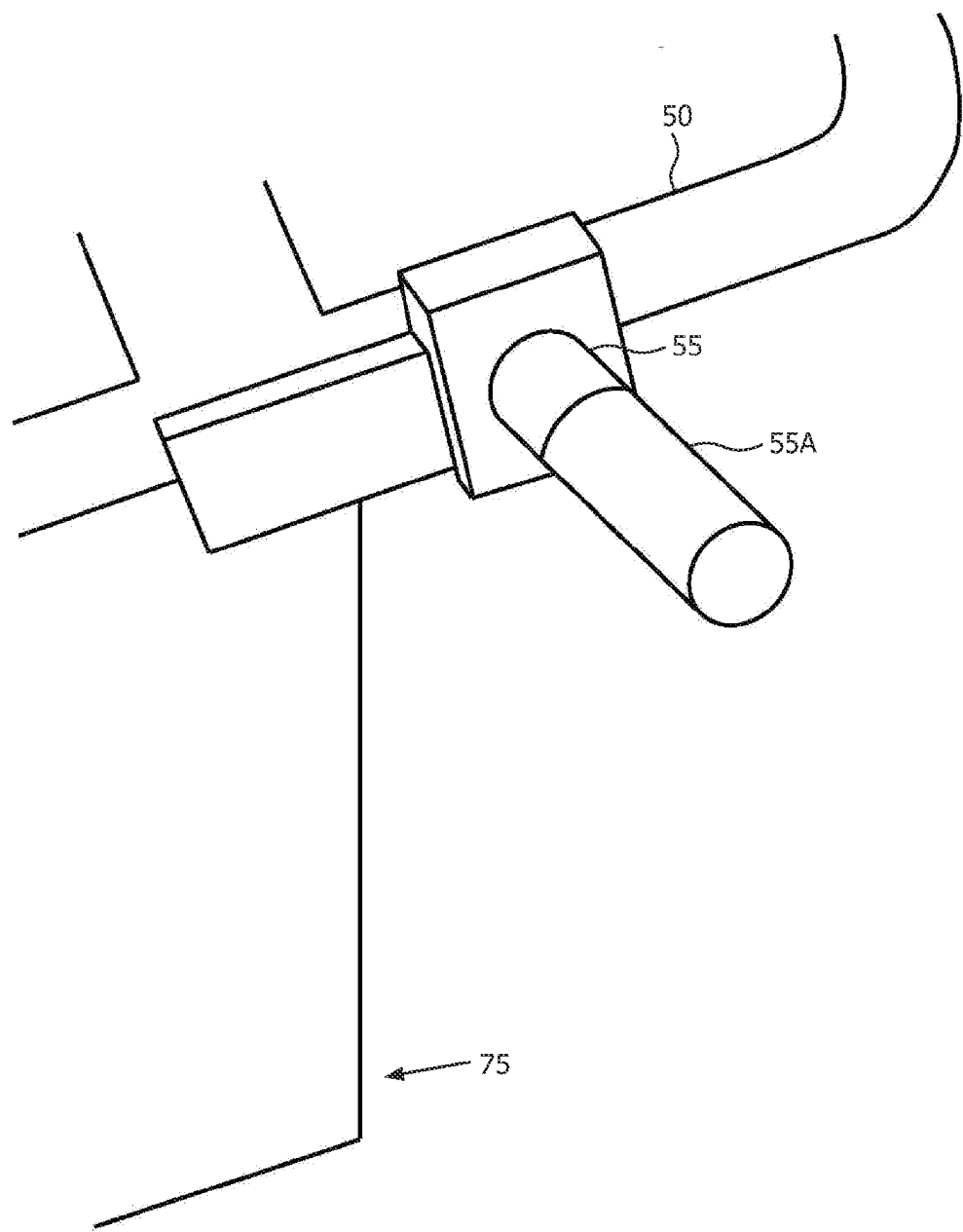
Figure 7B:
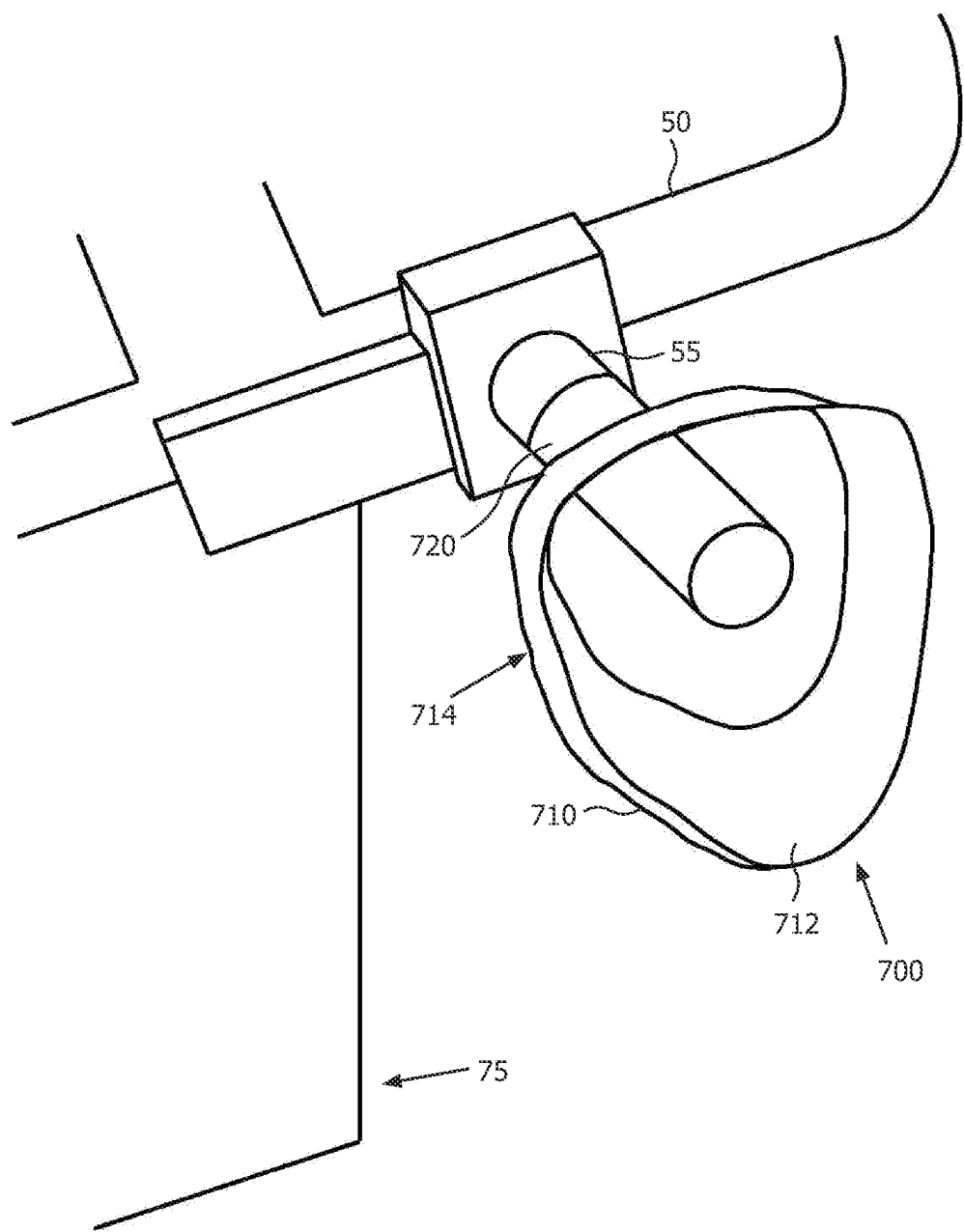
Figure 7C:
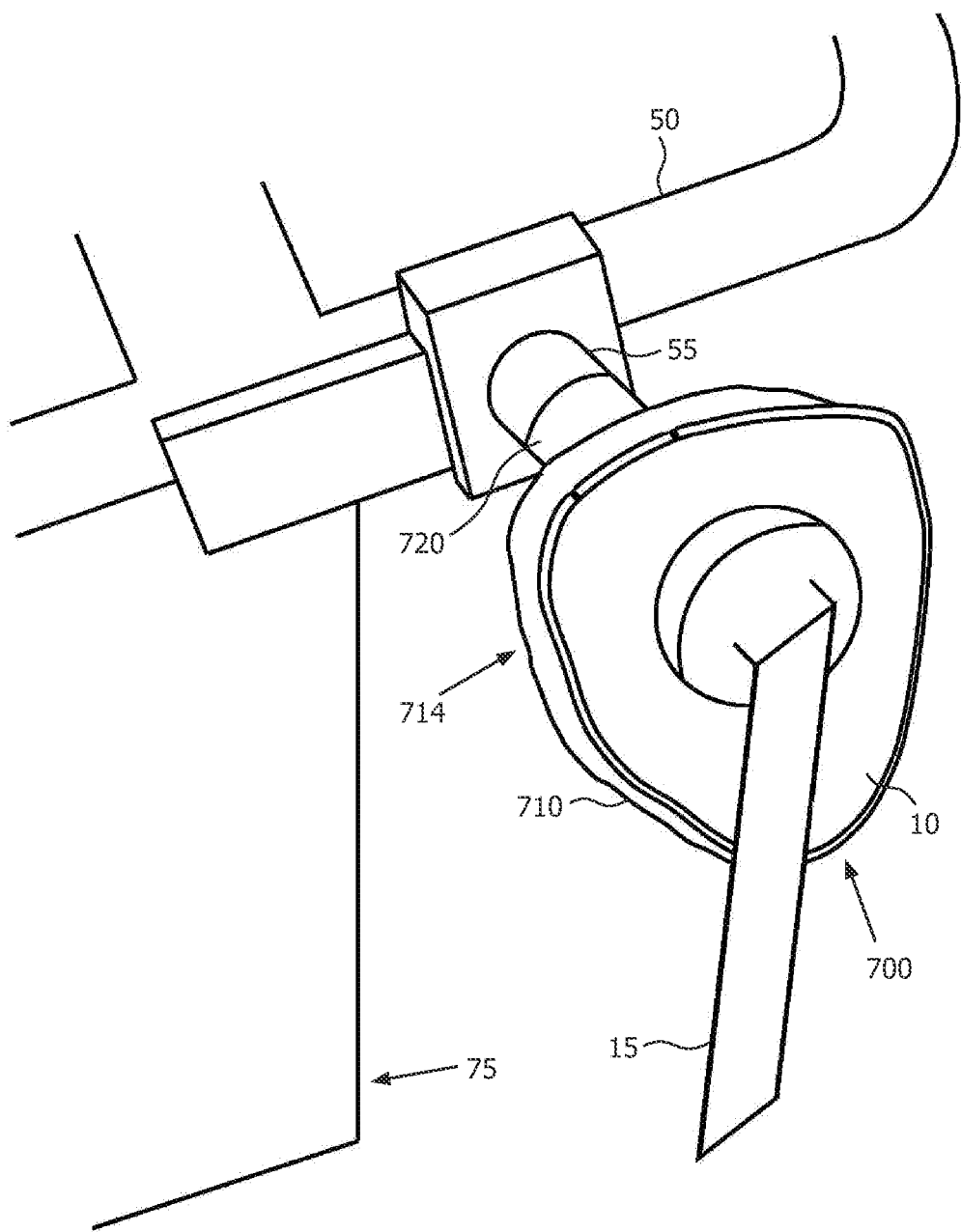

FIGS. 7A-C illustrate still another embodiment of a storage device for a ventilation mask.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

As used herein, the terms "approximately" and "nearly" each mean within 10%, and the term "substantially" means at least 75%.

Figure 3:
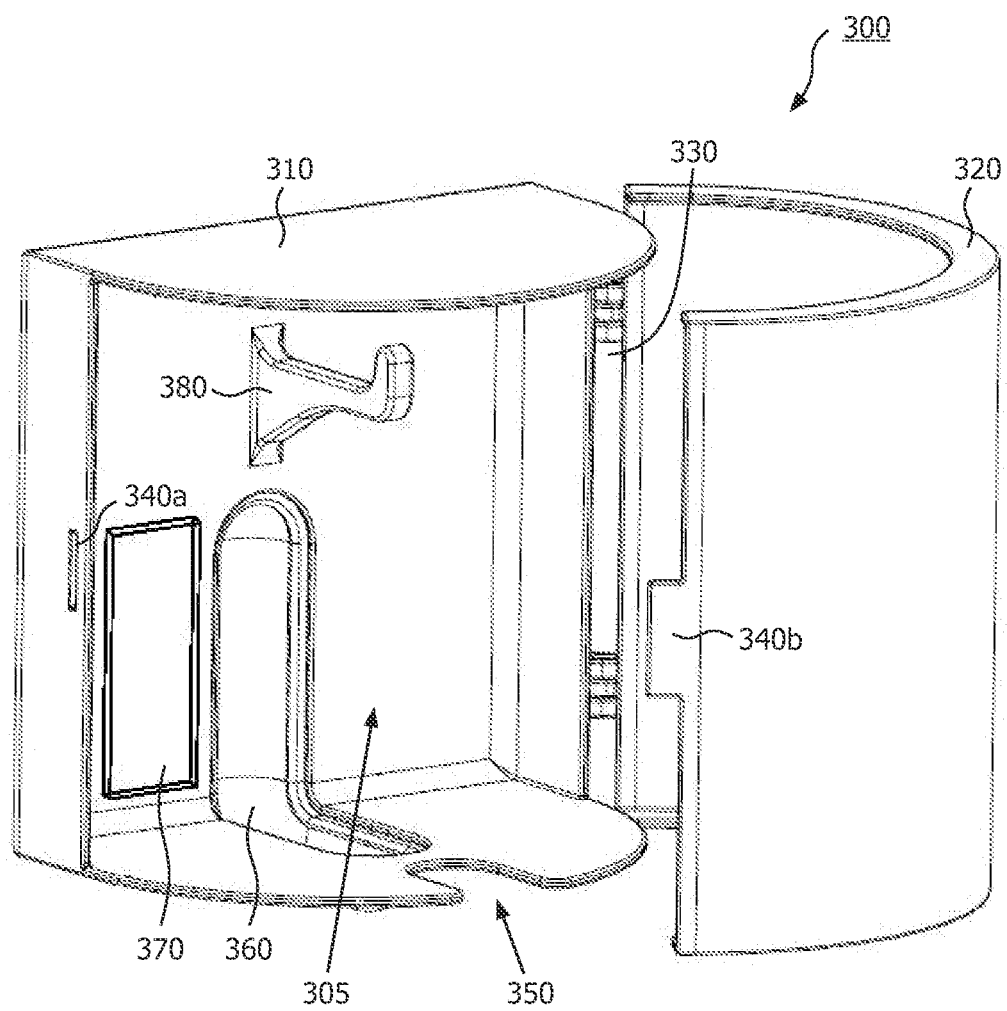
FIG. 3 illustrates one embodiment of a storage device for a ventilation mask.

FIG. 3 illustrates one embodiment of a storage device 300 for a ventilation mask. Storage device 300 is configured in the form of a closable container comprising a first body member 310, a second body member 320, a hinge 330, a clasping device comprising elements 340a and 340b, an opening or aperture 350, a connector 360, a disinfection system 370, and a hook 380.

In storage device 300, first body member 310 is a housing, and second body member 320 is a door.

Figure 1:
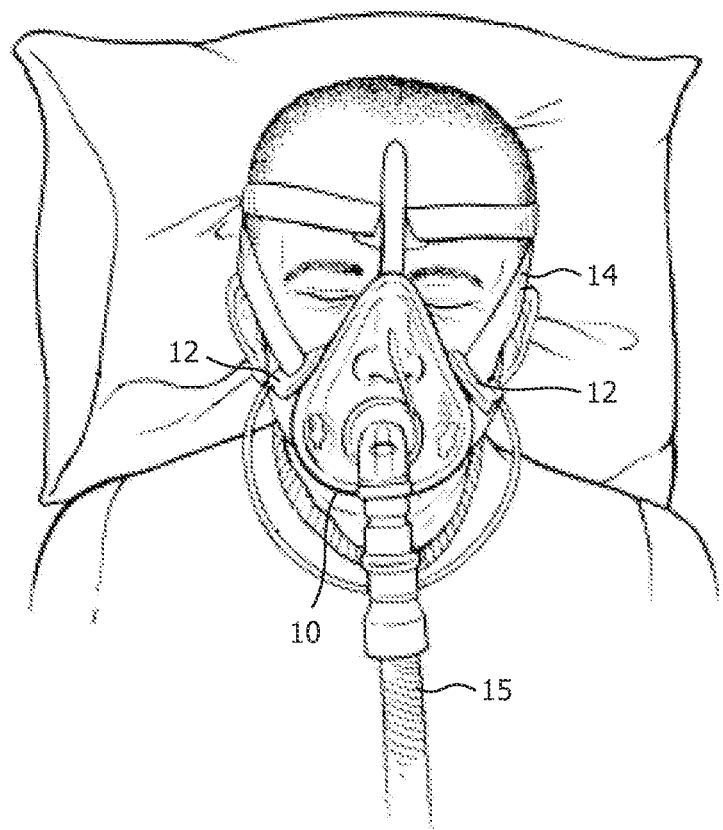
FIG. 1 illustrates a patient with a ventilation mask.
Figure 2:
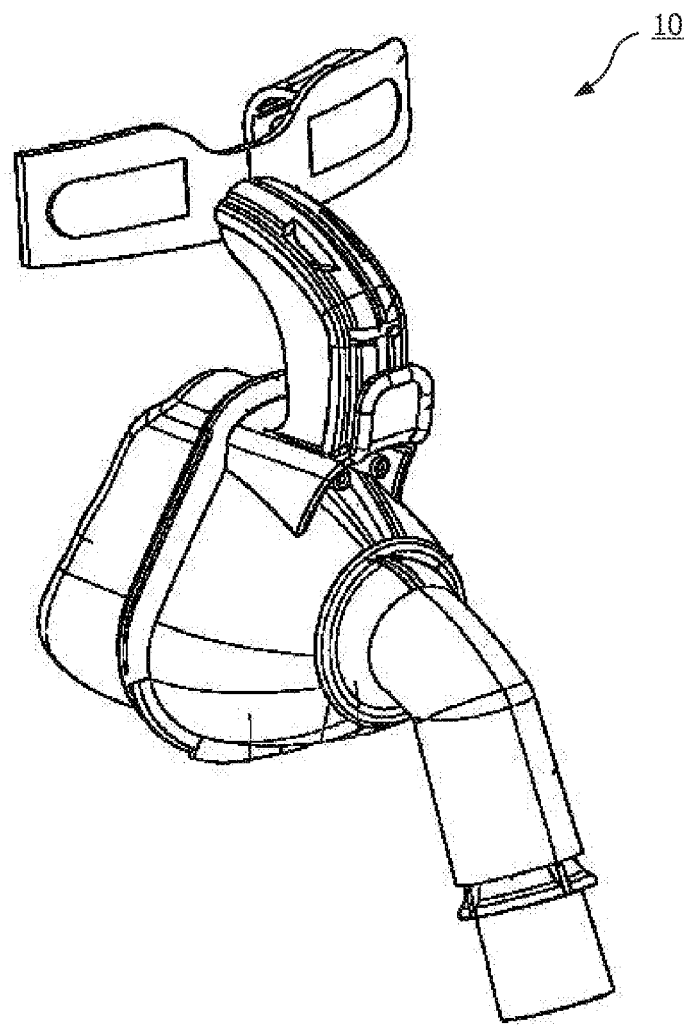
FIG. 2 illustrates an example of a ventilation mask.

Hinge 330 is connected to first body member 310 and to second body member 320 so that first body member 320 and second body member 320 can be brought together to define a substantially enclosed space 305 therebetween that is configured to receive a ventilation mask, for example ventilation mask 10 shown in FIG. 1. Beneficially, substantially enclosed space 305 is nearly enclosed or completely enclosed, with the exception of the apertures 350 and 360.

Clasping device element 340a is connected to first body member 310, and clasping device element 340b is connected to second body member 320 to hold first body member 310 and second body member 320 together when door 320 is closed and clasping device 340a/340b is engaged.

Aperture 350, and a similar aperture (not shown in FIG. 3) in door 320 are configured to permit circuit 15 (e.g., a flexible hose) to be connected to a ventilation mask 10 when door 320 is closed and ventilation mask 10 is disposed and stored within substantially enclosed space 305 of device 300.

Connector 360 is in the form of an aperture or slot which allows device 300 to be hung on a post or a hook that may be mounted on a ventilator or a ventilator cart on which ventilator is provided.

Other connectors can be employed for securing storage device 300 to a ventilator or ventilator cart or another suitable structure, including as non-limiting examples: a hook configured to be fitted around a portion of a ventilator or ventilator cart; a clamping device configured to be clamped to a portion of the ventilator or ventilator cart; a hollow post configured to be fitted over a post connected to the ventilator or ventilator cart; and a pair of connectors (similar to connectors 12 in FIG. 1) configured for a strap 14 or straps (e.g., straps fitted with VELCRO® or other hook-and-loop type attachments) to pass therethrough and thereby secure device 300 to the ventilator and ventilator cart. Of course other mechanisms for securing device 300 to a ventilator or ventilator cart—or even to another convenient secure location—could be employed.

Disinfection system 370 (which may be omitted in some embodiments) is configured to disinfect a ventilation mask 10 or 20 when ventilation mask 10 is disposed within substantially enclosed space 305 of device 300 when door 320 is closed. Beneficially, disinfection system 370 comprises an ultraviolet light, although it is conceivable that a chemical or other form of disinfectant may be employed. Beneficially, when door 320 is closed and/or when clasping device 340a/340b is engaged, a switch (not shown) is engaged to supply power to disinfection system 370 and begin an automatic disinfection cycle. In that case, device 300 may include a timer for stopping the sterilization cycle after a predetermined time period has elapsed. In addition or in the alternative, a manual switch may be provided on first or second member bodies 310 and 320 to initiate and/or terminate a disinfection cycle. Furthermore, although not shown in FIG. 3, one or more status indicator lights may be provided on housing 310 and/or door 320 to indicate when a disinfection cycle is in process, and/or when it is complete. Power may be supplied to disinfection system 370 by batteries mounted in housing 310, and/or by an electrical cable attached to a power supply strip or even to a power supply output of the ventilator.

Hook 380 a hook disposed on an interior surface of one of the first and second body members 310 and 320 (it is provided on housing 310 in the example shown in FIG. 3) is provided for securing the ventilation mask 10 within the enclosed space 305.

Beneficially, device 300 is intended to be reusable. In that case, beneficially device 300 is constructed from a durable plastic that is capable of being cleaned and disinfected/sterilized.

However, another embodiment of a device for storing a ventilation mask could be intended to be a disposable container.

Figure 4A:
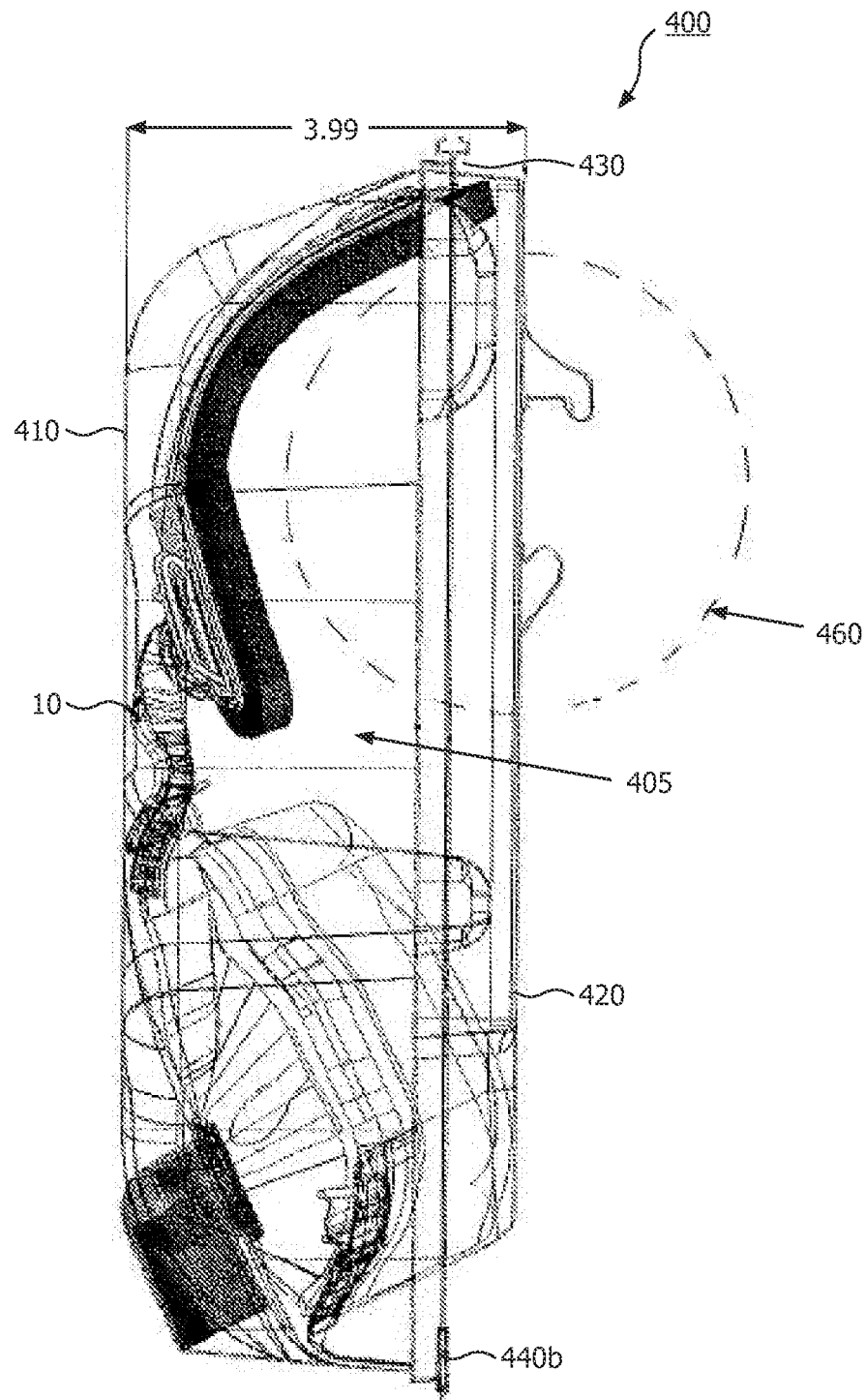
Figure 4B:
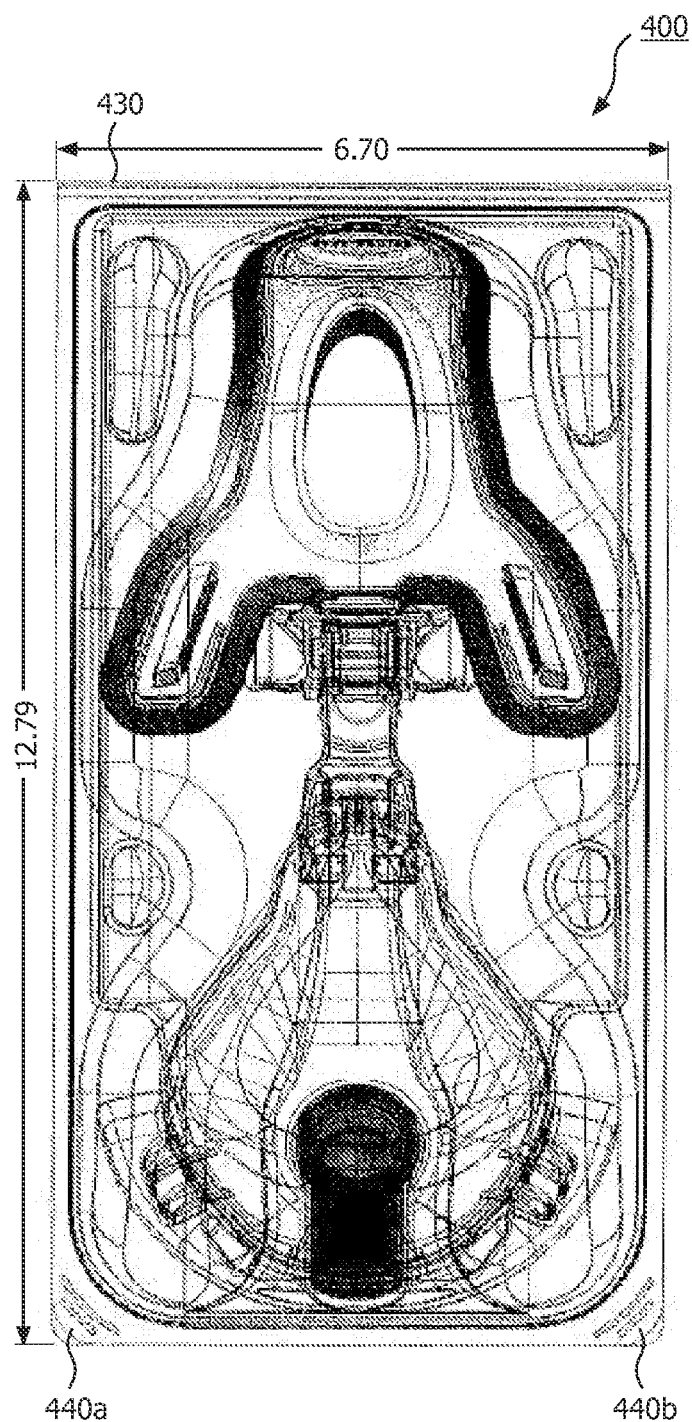
Figure 4C:
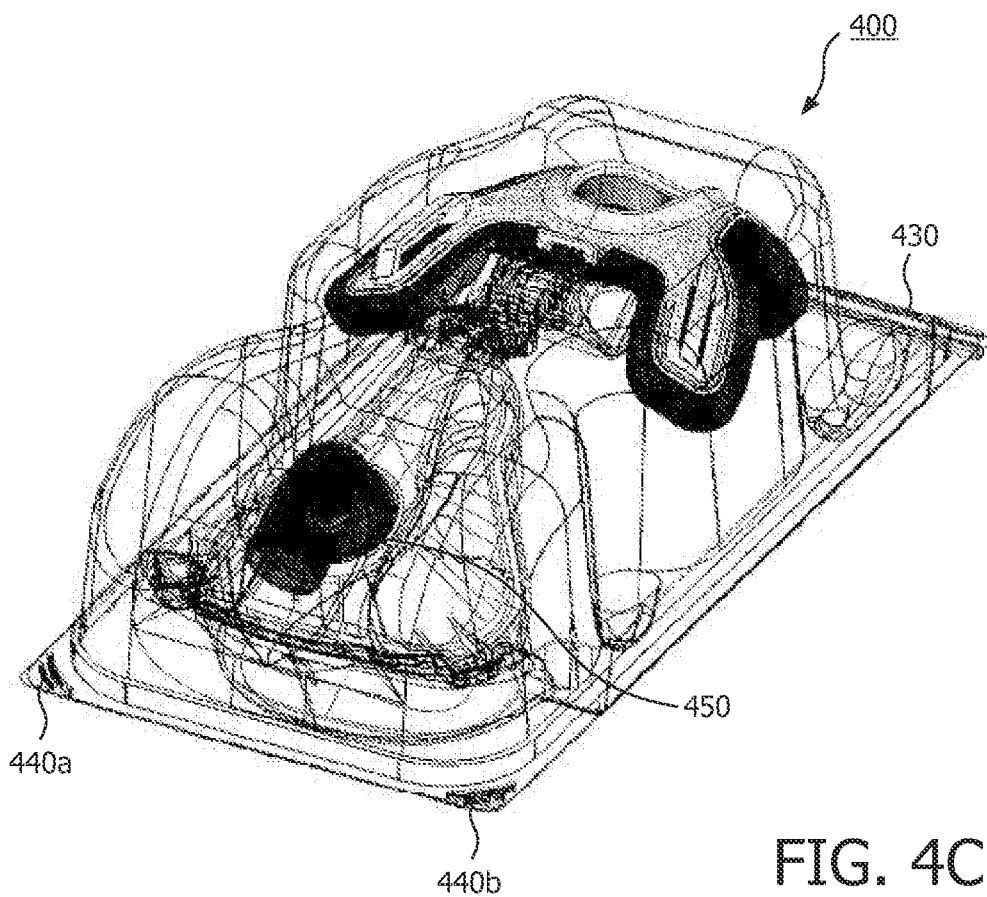
Figure 4D:
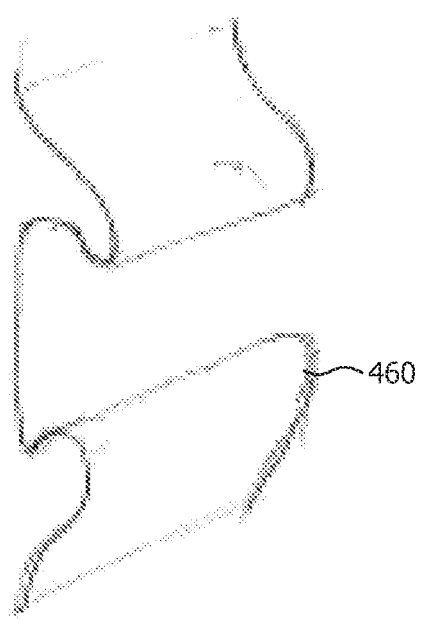

FIGS. 4A-D illustrate another embodiment of a storage device 400 for a ventilation mask. As illustrated in FIGS. 4A-D, device 400 is a "clam shell" structure comprising a first body member 410, a second body member 420, a hinge 430, a clasping device comprising elements 440a and 440b, an opening or aperture 450, and a connector 460. As shown in FIGS. 4A-C, device 400 is in a closed position defining a substantially enclosed space 405 and has a ventilation mask 10 stored therein.

Device 400 could be formed from a low cost material such as polystyrene, similar to containers used for packaging produce. Such a container could be inexpensively formed from a single sheet of material, and therefore could cost effectively be limited to use by just one patient and/or for a limited time period, and then disposed of and replaced.

Hinge 430 is connected to first body member 410 and to second body member 420 so that first body member 420 and second body member 420 can be brought together to define a substantially enclosed space 405 therebetween that is configured to receive a ventilation mask, for example ventilation mask 10. Beneficially, substantially enclosed space 405 is nearly enclosed or completely enclosed, with the exception of the aperture 450.

Clasping device elements 440a and 440b are configured to hold first body member 410 and second body member 420 together when clasping device 440a/440b is engaged.

Aperture 450 is configured to permit circuit 15 (e.g., a flexible hose) to be connected to a ventilation mask 10 or 20 when ventilation mask 10 is disposed within substantially enclosed space 405 of device 400.

Connector 460 is in the form of a clamping device.

Other connectors can be employed for securing storage device 400 to a ventilator or ventilator cart or another suitable structure, including as non-limiting examples: a hook configured to be fitted around a portion of a ventilator or ventilator cart; a clamping device configured to be clamped to a portion of the ventilator or ventilator cart; a hollow post configured to be fitted over a post connected to the ventilator or ventilator cart; and a pair of connectors (similar to connectors 12 in FIG. 1) configured for a strap or straps (e.g., straps fitted with VELCRO® or other hook-and-loop type attachments) to pass therethrough and thereby secure device 400 to the ventilator and ventilator cart. Of course other mechanisms for securing device 400 to a ventilator or ventilator cart—or even to another convenient secure location—could be employed.

In one embodiment, device 400 could also serve a dual purpose as the shipping container for ventilation mask 10, so that it would have a minimal impact on cost.

FIGS. 5A-B illustrate yet another embodiment of a storage device 500 for a ventilation mask. As illustrated in FIGS. 5A-B, device 500 is a "clam shell" structure comprising a first body member 510, a second body member 520, a hinge 530, a clasping device comprising elements 540a and 540b, and a connector 560 (the opening or aperture for the circuit that would be connected to a ventilation mask is not visible in FIGS. 5A-B. As shown in FIGS. 5A-B, device 500 is in an open position and hinge 530 would have to be manipulated to bring first body member 510 and second body member 530 together to define a substantially enclosed space 505 therebetween to receive and store a ventilation mask (not shown in FIGS. 5A-B). Beneficially, substantially enclosed space 505 is nearly enclosed or completely enclosed, with the exception of the aperture for connecting a circuit from the ventilation mask to the ventilator.

Device 500 is similar to device 400, so a detailed description thereof will not be repeated and only the differences will be highlighted. First, as noted above, device 500 is shown in FIGS. 5A-B in an open state without any ventilation mask stored therein, in contrast to device 400 which is shown in a closed state with ventilation mask 10 stored therein. Also, device 500 includes the connector 560 in the form of a hook or ring configured to be fitted around a portion of the one of the ventilator or ventilator cart.

FIG. 6 is another view of the ventilation mask storage device 500 of FIGS. 5A-B. FIG. 6 shows device 500 in a closed state with a ventilation mask 10 stored therein.

Through the use of storage devices 400, 500 and 600, a ventilation mask 10 may be secured in a safe and clean location when it is temporarily not being used, so that it does not fall onto the floor, or come into contact with a contaminated surface, is not exposed to airborne contaminants.

FIGS. 7A-C illustrate still another embodiment of a storage device 700 for a ventilation mask.

FIG. 7A shows a portion of a ventilation cart 75 for holding a ventilator (not shown). Ventilator cart 75 includes a railing 50 with a post 55 mounted thereon. It should be understood that the post 55 could be provided in a number of other arrangements and configurations, for example affixed to various locations on a ventilator or ventilator cart 75. Beneficially, post 55 has an indent or a raised feature 55A whose purpose will be described below.

FIG. 7B shows a device 700 mounted onto post 55. Device 700 includes a body member 710 having a first side 712 and second side 714 and a connector 720 provided on second side 714 of body member 710. First side 712 defines a recess therein that is configured to receive and hold a ventilation mask 10. Connector 720 is configured to attach device 700 to post 55. Beneficially, connector 720 is a hollow post, with the diameter of the hollow interior matched to the diameter of post 55 so that post 55 may be inserted into the hollow interior of hollow post 720. Beneficially, the interior surface of hollow post 720 has an indent or a raised feature (not shown) for engaging with feature 55A of post 55 to securely mount device 700 onto post 55.

FIG. 7C shows a ventilation mask 10 provided in a recess of first surface 712 of device 710. Through this arrangement, a ventilation mask 10 may be secured in a safe and clean location when it is temporarily not being used, so that it does not fall onto the floor, or come into contact with a contaminated surface, and to reduce exposure to airborne contaminants.

Many variations on device 700 are possible. For example, device 700 could include a hinge and a clamshell cover similar to devices 400 and 500. Also, instead of—or in addition to—the hollow post 720, device 700 could include any of the other connector types described above with respect to devices 300, 400 and 500.

It is possible to also combine several of the previously discussed embodiments. For example, a disposable container could serve as a "liner" and mate into a reusable container, thereby addressing any need for cleaning or disinfecting the reusable container. In addition, the reusable container could still utilize an integrated UV light disinfection system if the material chosen for the disposable container transmitted UV light or if the disposable container had a cut out for the UV light source.

A mask storage device as described above could be used with all devices that use a mask as an interface (e.g., invasive/noninvasive ventilators, noninvasive ventilators, CPAP devices, cough assist devices) including those marketed by for use in the hospital and home. Furthermore, a UV disinfection container such as device 300 may have applications for other devices that are reused at the bedside.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. A ventilation mask storage and disinfection device for storing and disinfecting a ventilation mask when not in use, comprising.
    a first body member including:
        a rear wall with a hook configured to hang the ventilation mask,
        a lower wall including a U-shaped aperture configured to receive a hose connected to the ventilation mask;
    a second body member connected to the first body member by a hinge, the second body member being configured to pivot on the hinge such that the first body member and the second body member can be brought together to define a substantially enclosed space therebetween that is configured to receive the ventilation mask hanging on the hook;
    a clasping arrangement connected to the first body member and the second body member to hold the first body member and the second body member together defining the substantially enclosed space when the clasping arrangement is engaged;
    a connector configured to attach the first body member to one of a ventilator or a ventilator cart such that the rear wall of the first body member is disposed substantially vertically; and
    a disinfection system configured to disinfect the ventilation mask when the ventilation mask is hanging on the hook within the substantially enclosed space.

2. The ventilation mask storage and disinfection device of claim 1, wherein the disinfection system includes an ultraviolet (UV) light.

3. The ventilation mask storage and disinfection device of claim 2, further comprising;
    a switch configured to selectively supply power to the UV light, the switch being configured to be engaged to supply the power to the UV light when the first body member and the second body member are brought together to define the substantially enclosed space therebetween.

4. The ventilation mask storage and disinfection device of claim 2, wherein the ultraviolet light is mounted to the first body member such that ultraviolet light irradiates the ventilator mask.

5. The ventilation mask storage and disinfection device of claim 1, wherein the first body member is a housing and the second body member is a door for the housing.

6. The ventilation mask storage and disinfection device of claim 1, wherein the first and second body members each comprise polysterene.

7. The ventilation mask storage and disinfection device of claim 1, further comprising:
    a third body member adjacent the first body member; and
    a fourth body member adjacent the second body member;
    wherein the third and fourth body members are configured such that when the first body member and the second body member are brought together to define the substantially enclosed space therebetween, then the third and fourth body members are nested inside the substantially enclosed space.

8. The ventilation mask storage and disinfection device of claim 1, wherein the connector is configured to engage and be supported by a portion of the one of the ventilator or the ventilator cart.

9. The ventilation mask storage and disinfection device of claim 1, wherein the connector includes a clamping device configured to be clamped to a portion of the one of the ventilator or the ventilator cart.

10. The ventilation mask storage and disinfection device of claim 1, wherein the connector includes an opening defined in the rear wall and configured to be placed on one of a hook and a peg.

11. The ventilation mask storage and disinfection device of claim 1, wherein the connector includes a hollow post configured to be fitted over a post connected to the one of the ventilator or the ventilator cart.

12. The ventilation mask storage and disinfection device of claim 1, wherein the connector includes a first connector and a second connector provided with at least one of the first and second body members, the first and second connectors being configured to attach the device to one of the ventilator or the ventilator cart by a strap pass through the first and second connectors.

13. The ventilation mask storage and disinfection device of claim 1, wherein the connector includes a hook configured to be fitted around a portion of the one of the ventilator or the ventilator cart.

14. The ventilation mask storage and disinfection device of claim 1, wherein the lower wall of the first body member has a substantially U-shaped periphery and wherein the first body member further includes:
   an upper wall with a U-shaped periphery.

15. The ventilation mask storage and disinfection device of claim 14, wherein the second body portion is substantially U-shaped.

16. The ventilation mask storage and disinfection device of claim 15, wherein the hinge is connected with the rear wall of the first body member and with an edge of the second body member.

17. In combination, a ventilator or ventilator cart and the ventilation mask storage and disinfection device of claim 1 connected with the ventilator or the ventilator cart.

18. In combination, a ventilation mask and the ventilation mask storage and disinfection device of claim 1.

19. The combination of claim 18, further including a hose extending through the first body member lower wall U-shaped aperture and connected with the ventilation mask.

20. The combination of claim 18, further including a ventilator or ventilator cart attached with the connector.

\* \* \* \* \*